US00PP23859P2

(12) United States Plant Patent
Heuger

(10) Patent No.: US PP23,859 P2
(45) Date of Patent: Aug. 27, 2013

(54) ***HELLEBORUS* PLANT NAMED 'COSEH 890'**

(50) Latin Name: ***Helleborus niger*×*Helleborus lividus***
Varietal Denomination: COSEH 890

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 13/385,156

(22) Filed: Feb. 6, 2012

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Kent L Bell
(74) *Attorney, Agent, or Firm* — C. A. Whealy

(57) ABSTRACT

A new and distinct cultivar of *Helleborus* plant named 'COSEH 890', characterized by its upright and uniformly mounded plant habit; uniform and freely flowering habit; dark green-colored leaves; long flowering period; single light yellow green-colored flowers that are tinged with greyed red and greyed purple; and good garden performance.

2 Drawing Sheets

Botanical designation: *Helleborus niger*×*Helleborus lividus.*

Cultivar denomination: 'COSEH 890'.

BACKGROUND OF THE INVENTION

The present invention relates to a new and distinct cultivar of *Helleborus* plant, botanically known as *Helleborus niger*× *Helleborus lividus*, and hereinafter referred to by the name 'COSEH 890'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2005 of an unnamed proprietary seedling selection of *Helleborus niger*, not patented, as the female, or seed, parent with an unnamed proprietary seedling selection of *Helleborus lividus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in February, 2008.

Asexual reproduction of the new *Helleborus* plant by divisions in a controlled greenhouse environment in Glandorf, Germany since March, 2008 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 890'.

These characteristics in combination distinguish 'COSEH 890' as a new and distinct *Helleborus* plant:

1. Upright and uniformly mounded plant habit.
2. Uniform and freely flowering habit.
3. Dark green-colored leaves.
4. Long flowering period.
5. Single light yellow green-colored flowers that are tinged with greyed red and greyed purple.
6. Good garden performance.

Compared to plants of the parent selections, plants of the new *Helleborus* are more uniformly mounded and are more uniformly and freely flowering.

Plants of the new *Helleborus* can be compared to plants of *Helleborus niger*×*Helleborus lividus* 'COSEH 700', disclosed in U.S. Plant Pat. No. 21,003. In side-by-side comparisons conducted in Glandorf, Germany, plants of the new *Helleborus* differed from plants of 'COSEH 700' in leaf and flower color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant. The photograph on the first sheet comprises a side perspective view of a typical flowering plant of 'COSEH 890' grown in a container. The photograph on the second sheet is a close-up view of a typical flower of 'COSEH 890'.

DETAILED BOTANICAL DESCRIPTION

The aforementioned photographs and following observations, measurements and values describe plants grown during the winter in 17-cm containers in a glass-covered greenhouse in Glandorf, Germany and under environmental conditions and cultural practices which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus lividus* 'COSEH 890'.

Parentage:

*Female, or seed, parent*.—Unnamed proprietary seedling selection of *Helleborus niger*, not patented.

*Male, or pollen, parent*.—Unnamed proprietary seedling selection of *Helleborus lividus*, not patented.

Propagation:

*Type*.—By tissue culture.

*Time to initiate roots*.—About two months at 12° C.

*Time to produce a rooted young plant*.—About six months at 4° C. to 15° C.

*Root description*.—Thick to thin, fleshy; white to brown in color.

*Rooting habit*.—Sparse.

Plant description:

*Plant form and growth habit*.—Herbaceous perennial; upright and uniformly mounding plant habit with flowers held just above the foliar plane; plant shape is flattened globular; moderately vigorous growth habit.

*Plant height*.—About 39.9 cm.

*Plant diameter* (*area of spread*).—About 67.8 cm.

Foliage description:

*Arrangement*.—Leaves arranged in a basal rosette; leaves palmately compound with five leaflets per leaf.

*Leaf length*.—About 15.5 cm.

*Leaf width*.—About 18.1 cm.

*Leaflet length*.—About 9.7 cm.

*Leaflet width*.—About 4.4 cm.

*Leaf shape*.—Palmate; orbicular in outline.

*Leaflet shape*.—Elliptic to ovate or obovate.

*Leaflet apex*.—Acute.

*Leaflet base*.—Attenuate.

*Leaflet margin*.—Sharply serrate.

*Leaflet texture, upper and lower surfaces*.—Smooth, glabrous; leathery.

*Leaflet venation pattern*.—Pinnate.

*Leaflet color*.—Developing leaves, upper surface: Between 143C and 144A. Developing leaves, lower surface: Close to 148A. Fully developed leaves, upper surface: Darker than between N137A and 147A; venation, close to 144A to 144B; at the base, close to 200A to 200B. Fully developed leaves, lower surface: Between 147A to 147B and 197A; venation, between N186C and 187A.

*Petiole*.—Length: About 12.1 cm. Diameter: About 5 mm. Texture, upper and lower surfaces: Smooth, glabrous. Color, upper and lower surfaces: Close to 147C to 147D, heavily tinged and dotted with between N186C and 187A.

Flower description:

*Flower shape and habit*.—Single rotate flowers arranged in terminal and axillary cymes; freely and uniform flowering habit with about 100 flowers and flower buds developing per plant; flowers facing outwardly to slightly nodding and slightly upright.

*Fragrance*.—None detected.

*Natural flowering season*.—Plants begin flowering about ten months after planting; long flowering period, plants flower from late winter to early spring in Germany.

*Flower longevity on the plant*.—About ten days; flowers not persistent.

*Flower buds*.—Length: About 1.8 cm. Diameter: About 1.4 cm. Shape: Broadly ovate. Color: Close to 150D.

*Inflorescence height*.—About 38.1 cm.

*Inflorescence diameter*.—About 28.3 cm.

*Flower diameter*.—About 6.3 cm.

*Flower depth* (*height*).—About 3 cm.

*Petals*.—Transformed into nectaries.

*Sepals*.—Quantity and arrangement: Five arranged in a single whorl. Length: About 3.2 cm. Width: About 2.3 cm. Shape: Broadly ovate to broadly elliptic. Apex: Obtuse. Margin: Entire. Texture, upper and lower surfaces: Smooth, glabrous. Color: When opening, upper surface: Close to 145C to 145D. When opening, lower surface: Close to 150D; towards the base, close to 145C. Fully opened, upper surface: Close to 145D tinged with close to 186C to 186D; towards the base, close to 145B; with development, color becoming closer to 147C shaded with close to 176C to 176D. Fully opened, lower surface: Close to 145C strongly tinged with between 181D and 185D.

*Peduncles*.—Strength: Moderately strong. Length: About 31.8 cm. Diameter: About 6 mm. Aspect: About 30° from vertical. Texture: Smooth, glabrous. Color: Close to 145D moderately dotted with between 181A and 182A.

*Pedicels*.—Strength: Moderately strong. Length: About 2 cm. Diameter: About 1.5 mm. Aspect: Erect to about 30° from the peduncle axis. Texture: Smooth, glabrous. Color: Close to 145C.

*Reproductive organs*.—Stamens: Quantity per flower: About 50. Filament length: About 1.6 cm. Filament color: Close to 157D. Anther shape: Reniform. Anther length: About 1.5 mm. Anther color: Close to 150C. Pollen amount: Scarce. Pollen color: Close to 158D. Pistils: Quantity per flower: About six. Pistil length: About 1.2 cm. Stigma shape: Club-shaped. Stigma color: Close to 157C. Style length: About 1.1 cm. Style color: Close to 157C. Ovary color: Close to 157A. Nectaries (transformed petals): Quantity per flower: About 13. Length: About 8 mm. Diameter, apex: About 2 mm. Diameter, base: About 1 mm. Shape: Flattened triangular. Color: Close to 144C; towards the apex, close to N144B.

*Seeds and fruits*.—Seed and fruit development have not been observed on plants of the new *Helleborus*.

Garden performance: Plants of the new *Helleborus* have been observed to have good garden performance and to tolerate rain and wind; plants of the new *Helleborus* have been observed to tolerate high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 890' as illustrated and described.

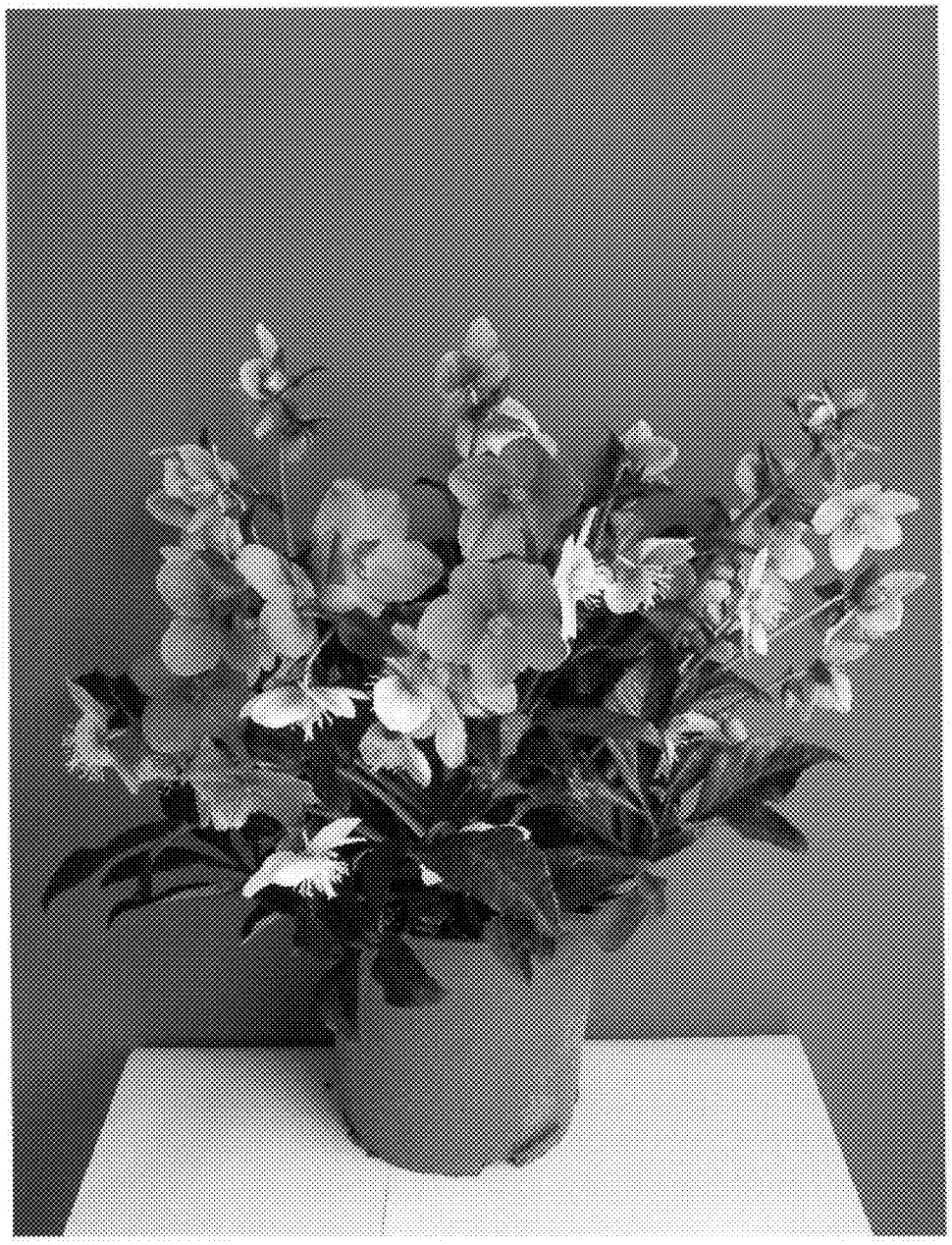

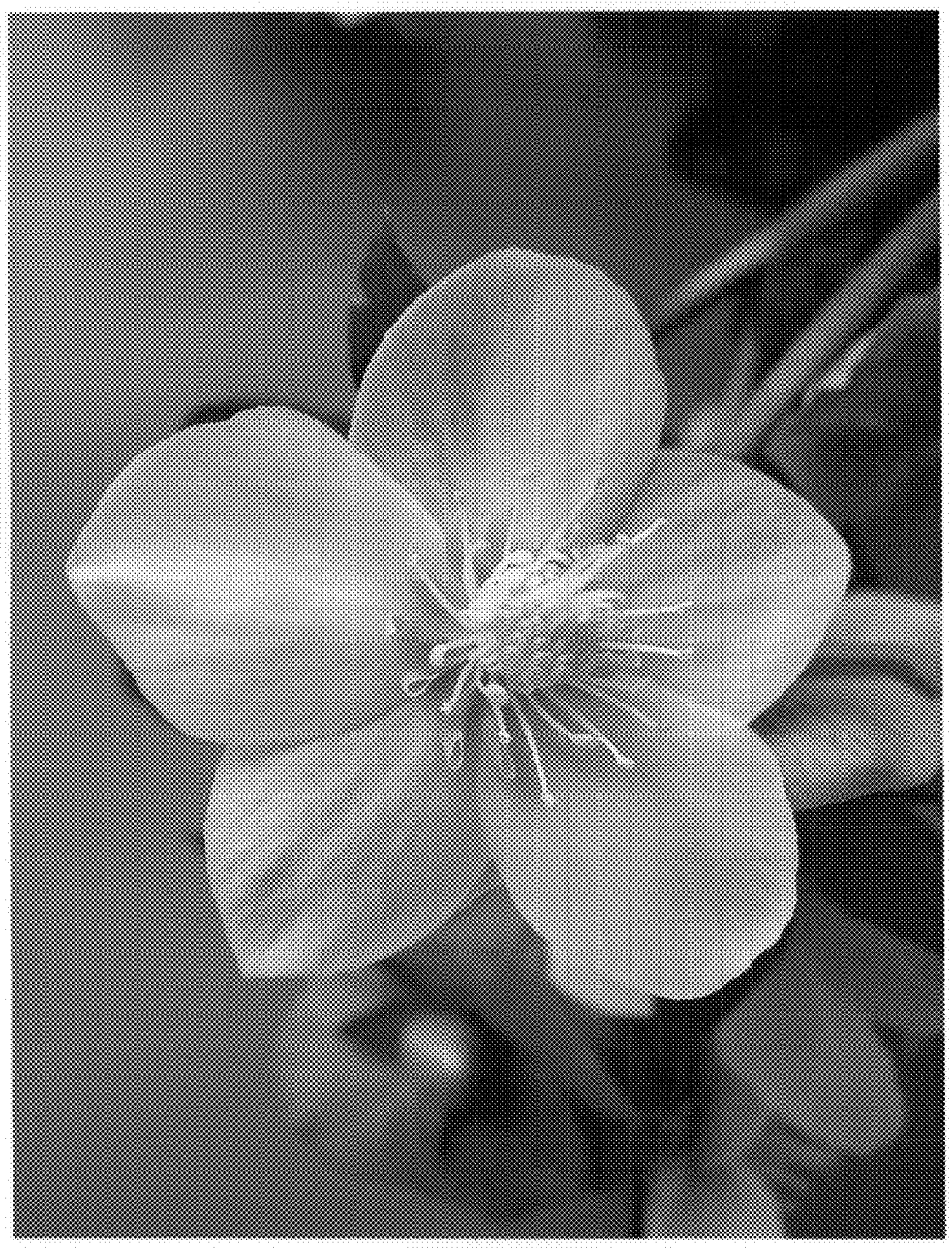

* * * * *